United States Patent
Yacoub et al.

(10) Patent No.: US 9,878,073 B2
(45) Date of Patent: Jan. 30, 2018

(54) NITRIC OXIDE-ELUTING BIORESORBABLE STENTS FOR PERCUTANEOUS CORONARY INTERVENTIONS

(71) Applicant: HEART BIOTECH LIMITED, London (GB)

(72) Inventors: Magdi Habib Yacoub, London (GB); Ibrahim El-Sherbiny, 6th of October (EG)

(73) Assignee: HEART BIOTECH LIMITED, London (GB)

( * ) Notice: Subject to any disclaimer, the term of this patent is extended or adjusted under 35 U.S.C. 154(b) by 0 days.

(21) Appl. No.: 15/133,353

(22) Filed: Apr. 20, 2016

(65) Prior Publication Data
US 2016/0303294 A1    Oct. 20, 2016

(30) Foreign Application Priority Data
Apr. 20, 2015    (GB) .................... 1506655.8

(51) Int. Cl.
| | |
|---|---|
| *A61F 2/82* | (2013.01) |
| *A61L 31/14* | (2006.01) |
| *A61L 31/02* | (2006.01) |
| *A61L 31/10* | (2006.01) |
| *A61L 31/16* | (2006.01) |
| *A61F 2/958* | (2013.01) |
| *A61L 31/04* | (2006.01) |
| *A61L 31/06* | (2006.01) |

(52) U.S. Cl.
CPC ............. *A61L 31/148* (2013.01); *A61F 2/82* (2013.01); *A61F 2/958* (2013.01); *A61L 31/022* (2013.01); *A61L 31/048* (2013.01); *A61L 31/06* (2013.01); *A61L 31/10* (2013.01); *A61L 31/145* (2013.01); *A61L 31/146* (2013.01); *A61L 31/16* (2013.01); *A61L 2300/114* (2013.01); *A61L 2300/416* (2013.01); *A61L 2300/624* (2013.01); *A61L 2420/02* (2013.01); *A61L 2420/06* (2013.01)

(58) Field of Classification Search
CPC .. A61L 31/148; A61F 2/82; A61F 2/86; A61F 2/89; A61F 2/90; A61F 2/91; A61F 2/915
See application file for complete search history.

(56) References Cited

U.S. PATENT DOCUMENTS

| | | | |
|---|---|---|---|
| 2007/0148251 A1 | 6/2007 | Hossainy et al. | |
| 2007/0243224 A1* | 10/2007 | Ludwig ............... | A61K 31/198 424/423 |
| 2008/0317813 A1 | 12/2008 | Craig et al. | |

OTHER PUBLICATIONS

Gogas, B. D. Bioresorbable Scaffolds for Percutaneous Coronary Interventions. Global Cardiology Science and Practice, 2014.
Voûte, M. T.; Gonçalves, F. M. B.; van de Luijtgaarden, K. M.; Nulent, C. G. K; Hoeks, S. E.; Stolker, R. J.; Verhagen, H. J. Stent Graft Composition Plays a Material Role in the Postimplantation Syndrome. Journal of vascular surgery 2012, 56, 1503-1509.
Acharya et al., Optimization of cardiovascular stent against restenosis: factorial design-based statistical analysis of polymer coating conditions, PLos One, 2012, 7(8), e43100; http://journals.plos.org/plosone/article?id=10.1371/journal.pone.0043100.
Search Report, dated Nov. 9, 2015, issued in priority UK Application No. GB1506655.8.
Mohamed et al., a New NO-Releasing Nanoformulation for the Treatment of Pulmonary Arterial Hypertension, J. Cardiovascualr Translation Research, 9:162-164 (2016).

* cited by examiner

*Primary Examiner* — Christopher D Prone
*Assistant Examiner* — Suba Ganesan
(74) *Attorney, Agent, or Firm* — Saul Ewing Arnstein & Lehr LLP

(57) ABSTRACT

The invention involves bioresorbable stents which elute nitric oxide (NO). The stent is comprised of three main key design elements: a bioresorbable scaffold, a bioresorbable polymeric coating layer(s), and NO-releasing nanoparticles incorporated in the bioresorbable polymeric coating layer, and optionally also in the scaffold. The NO-releasing nanoparticles are made of nontoxic biocompatible and biodegradable materials; for example a chitosan polymer and optionally a sugar.

23 Claims, 2 Drawing Sheets

NITRIC OXIDE-ELUTING BIORESORBABLE STENTS FOR PERCUTANEOUS CORONARY INTERVENTIONS

CROSS-REFERENCE TO RELATED APPLICATIONS

This application is based on, and claims priority to, UK Application No. 1506655.8, filed Apr. 20, 2015, the entire contents of which being fully incorporated herein by reference.

FIELD OF THE INVENTION

The present invention relates to bioresorbable stents which elute nitric oxide (NO).

BACKGROUND TO THE INVENTION

A stent is a physical support in the form of a hollow mesh tube that is used in many cases to maintain adequate flow in body passages including cardiovascular, urethral, esophageal, biliary, prostatic or pancreatic vessels.

The geometrical design of a stent plays a major role in its strength, performance and elasticity. Design of stents aims at getting the highest radial resistive force possible and the lowest chronic outward force possible. A range of different stent patterns are known to the skilled person, and an appropriate pattern may be selected for a given use.

Traditionally, stents were fabricated of bare metals as platinum, chromium or stainless steel. However, the permanent presence of stents in the injury site after complete recovery of the vascular functioning leads to late complications including late stenosis and late lesion revascularization.[1] Intensive research effort has been performed to develop more advanced stents as drug eluting stents. However, Post-Implementation Syndrome (PIS) is still a common complication of stent implementation which is defined as fever and transient elevation in inflammatory biomarkers. Mechanisms lying behind PIS are still unknown; however it seems related to the type of material used for fabrication of stents. As a result, efforts were directed to the development of bioresorbable stents (also referred to as biodegradable or bioabsorbable stents; the terms are used interchangeably herein) to avoid unnecessary presence of the stent after an adequate recovery period that may vary starting from about 6 months.

Several materials are currently used to fabricate cardiovascular stents. Among these materials are woven polyesters and expanded polytetrafluoroethylene. It was found that polytetrafluoroethylene induces less inflammation when compared to woven polyesters.[2] A common metal stent is made of nitinol which is a mixture of nickel and titanium.

Conventional stents are unable to inhibit overgrowth of smooth muscle and extracellular matrix which eventually leads to narrowing of blood vessels. One of the approaches investigated to overcome such problem is to develop biodegradable stents. One of the most commonly used materials for biodegradable stents is polylactide which is degraded into water and $CO_2$ and thus, its implementation is inert to the body. Magnesium is also used for biodegradable stents in the form of various alloys, with or without additional coatings to decrease the degradation rate. However, the use of biodegradable stents is still limited due to many unsettled considerations. These include for instance; 1—incomplete endothelialization which may lead to increased thrombosis, 2—fragmentation of the stent by partial degradation that may release particles that can induce thrombosis, and 3—severe inflammation or fibrosis that may block the stented area. On the other hand, early investigations regarding the use of biodegradable stents showed good biocompatibility with minimal complications.

The versatility of the polymers used in stents allowed the development of bioresorbable drug eluting stents which release various drugs including heparin, antithrombotic and anti-inflammatory agents. The first drug eluting stent was approved for clinical use in 2003 and it was composed of 50/50% mixture of poly(ethylene-co-vinylacetate) (PEVA) and poly(butyl methacrylate) (PBMA) which is a biostable stent and was loaded with sirolimus which is a potent immunosuppressant and antiproliferative agent.

Although antiproliferative drugs are commonly incorporated into drug eluting stents, they do not provide an optimal solution to prevent post-implementation stenosis. These drugs inhibit the overgrowth of smooth muscle cells; however they also inhibit the re-growth of endothelial cells and endothelium healing. Incomplete endothelium and its inability to heal lead to endothelium dysfuction and remodeling. This observation motivated the search for drug eluting stents that allow adequate endothelial recovery while inhibiting stenosis. Another key factor in stenosis is the adhesion of platelets on the stent surface since after platelet adhesion and aggregation, α-granules are released containing P-selectin which induces more aggregation and thrombus formation. Thus an important goal of designing stent materials is to inhibit platelet adhesion to its surface.

BRIEF SUMMARY OF THE INVENTION

The present invention involves, for the first time, the development of multifunctional nitric oxide (NO)-eluting bioresorbable stents that elute therapeutic levels of NO in a controlled and sustained manner, and then bioresorb naturally into the body leaving no permanent stent. The stent is comprised of three main key design elements: a bioresorbable scaffold, a bioresorbable polymeric coating layer(s), and NO-releasing nanoparticles incorporated in the bioresorbable polymeric coating layer, and optionally also in the scaffold.

The NO-releasing nanoparticles are made of nontoxic biocompatible and biodegradable materials; preferably comprising a polymer and optionally a sugar. Preferably the polymer is a hydrogel polymer, and/or a swellable polymer. The polymers include, but are not limited to, chitosan, polyethylene glycol (PEG), and polyvinylpyrolidone (PVP). The sugars include, but are not limited to, sucrose, trehalose dehydrate, tagatose, and glucose. A preferred sugar is glucose. The nanoparticles may also comprise sodium tripolyphosphate. In a preferred embodiment, the nanoparticles comprise chitosan, polyethylene glycol (PEG), and polyvinylpyrolidone (PVP). The nanoparticles may also comprise an NO-donor, for example a nitrite, preferably sodium nitrite. Other NO donors include, but are not limited to, organic nitrates, nitrite salts, s-nitrosoglutathione (GSNO), and S-Nitrosothiols The sugars are used to perform thermal reduction of the NO-donor to generate therapeutic levels of NO in a controlled and sustained way. The NO-releasing nanoparticles are entrapped either in the coating layer(s), or in both the main scaffold and the coating layer(s) to continue releasing the NO for longer time.

The coating and/or the scaffold of the NO-eluting bioresorbable stents are made of a variety of biodegradable polymers of different molecular weights including, but not limited to, poly(ethylene-co-vinylacetate) (PEVA), poly(butyl methacrylate) (PBMA), poly (L-lactide) (PLLA), poly (D-lactide) (PDLA), poly (D,L-lactide) (PDLLA), poly(3-hydroxybutyrate), poly(4-hydroxybutyrate), poly(glycolic acid), polycaprolactone, polyethylene oxide, tyrosine derived polycarbonates, and polyanhydride esters of salicylic acid or a combination of two or more of said polymers. The coating and scaffold may each be made from said biodegradable polymers; each may be made from a different polymer, or from the same polymer.

The scaffold is preferably porous; this allows incorporation of NO-eluting nanoparticles into the scaffold.

In certain embodiments, the scaffold may be a biodegradable metal scaffold, for example comprising a biodegradable magnesium alloy.

The invented NO-eluting bioresorbable stent allows a sustained release of NO for a long time (from about 2-24 months) as the NO-releasing nanoparticles may be incorporated in both the stent's core and in the outer coating layer(s). Incorporating the nanoparticles in only the outer coating layer will provide for a shorter period of NO release, as this will break down sooner than the core. In addition, the invented stent offers many other unique active advantages. These include, but are not limited to, (a) immediate and sustained dilatation on the microvascular bed, (b) re-endothelial ideation to the coronary, (c) anti-inflammatory effect, (d) inhibition of smooth muscle proliferation, and (e) anti-thrombotic effect through its action on platelets.

In addition to the incorporated NO-eluting nanoparticle, the stent could also contain other therapeutic agents in the stent scaffold and/or the coating layer(s). These include, but are not limited to, everolimus, tacrolimus, paclitaxel, and sirolimus. These may be incorporated into the nanoparticle, or into the stent itself.

The NO-eluting bioresorbable stents are designed in such a way to allow good mechanical properties which are critical to its function as a support for the vascular system. The skilled person will be aware of suitable physical arrangements for different types of stent, and in particular suitable mesh patterns.

The stent may be provided in combination with a delivery catheter. The stent may be self-expanding, or the catheter may comprise an expansion device; for example, the catheter may be a balloon catheter.

In addition, the fabrication of the NO-eluting bioresorbable stent is achieved using techniques that maintain the stability of the incorporated NO-releasing nanoparticles. This could be achieved by many methods, although preferred techniques include "Particulate-Extrusion Leaching Technique (PELT)", "Controlled Expansion of Saturated Polymers (CESP)", and "Dip Coating (DC)". In the PELT, a salt such as NaCl of appropriate size is dispersed in the stent scaffold's polymer solution. The polymer is extruded through a suitable piston. The solvent is then allowed to evaporate completely. The dispersed salt particles are then dissolved in distilled water leaving a porous structure according to the amount of the added salt. The stent is then coated with a bioactive layer using another polymer solution (containing either the NO-releasing nanoparticles, or the NO-releasing nanoparticles and another bioactive agent). In the CESP, which is a useful technique for manipulation of polymers at relatively low temperature allowing the incorporation of thermo-sensitive bioactive agents such as the incorporated NO-releasing nanoparticles, the selected polymeric materials are processed under inert atmosphere as $CO_2$ at high pressure of around 50 bar. The applied high pressure leads to the absorption of $CO_2$ into the polymer until saturation. This leads to considerable reduction in the glass transition temperature which consequently allows manipulation of the polymer and incorporated bioactive substances (either the NO-releasing nanoparticles, or the NO-releasing nanoparticles and another bioactive agent) at relatively low temperatures of about 50° C. Then, upon removing the pressure, the polymer expands in the mold cavity, and the $CO_2$ is finally removed which returns the polymer to its normal state with the normal glass transition temperature.

In the DC method, the formed polymeric scaffold is coated by another selected polymer containing the NO-releasing nanoparticles or the NO-releasing nanoparticles and another bioactive agent, through repeatedly dipping into the coating polymer solution till the desired thickness of the coat is reached.

DETAILED DESCRIPTION OF THE INVENTION

Figure 1A:
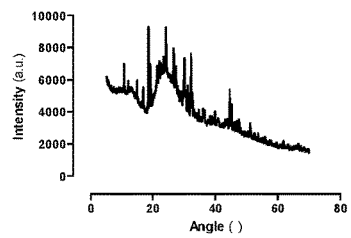
FIGS. 1A and 1B show the nanoparticles characterised by powder X-ray diffraction (FIG. 1A) and themogravimetric analysis (FIG. 1B).

The present invention provides novel type of drug-eluting bioresorbable stents for percutananeous coronary interventions.

Background art which may be of benefit in understanding the invention includes:

Mohamed, N. A., Ahmetaj-Shala B., Harrington, L. S., Kirkby, N. S., Reed, D. M., Lickiss, D. M., Davies, R. P., Wojciak-Stothard, B., Chester, A. H., El-Sherbiny, I. M., Mitchell, J. A., & Yacoub, M. (2015). Early pre-clinical results of a novel NO-nanoformulation for the treatment of pulmonary hypertension (PHT). The 8th PVRI Annual World Congress, January, 15-18, Guangzhou, China.

Reference to these publications should not be taken as an admission that the contents of any particular document are relevant prior art. However, the skilled person is referred to the above reference for details of ways in which NO-releasing nanoparticles may be produced.

Various preliminary studies (such as the referred to in the citation listed above) performed with regard to developing long acting NO-eluting nanoparticles for different purposes support the proposal that incorporating NO-releasing nanoparticles in a bioresorbable polymeric stent will allow release of therapeutic levels of NO for long time (from about 2-24 months) as the NO-releasing nanoparticles may be incorporated in both the stent's core and in the outer coating layer(s). Remarkably, the preliminary data has shown that the invented stent offers many unique active advantages. These include, but not limited to, (a) immediate and sustained dilatation on the microvascular bed,
(b) re-endothelial ideation to the coronary,
(c) anti-inflammatory effect,
(d) inhibition of smooth muscle proliferation, and
(e) anti-thrombotic effect through its action on platelets.

Experiments

The NO-releasing nanoparticles were made of a combination of polymers including, but not limited to, chitosan of low molecular weight, PEG 400, polyvinyl pyrolidone (PVP), and other materials such as glucose, sucrose, alginate, sodium tripolyphosphate, and tetramethylorthosilicate. The sugar was used to perform a thermal reduction of the loaded NO-donor, sodium nitrite ($NaNO_2$) to generate NO gas. The NO remains entrapped inside the developed nanoparticles powder until undergoing a sustained release because of the swelling of the prepared hydrogel-based nanoparticles upon exposure to moist environment. Various nanoparticles were prepared with different concentrations of the NO-donor, sodium nitrite. For instance, the sample (NO-Polym-4) was prepared as follow: Sodium nitrite solution was prepared (1 g in 30 mM PBS at pH 7.5). Then, D-glucose was added at 40 mg D-glucose/mL of sodium nitrite solution followed by addition of PVP (6.25 mg) with stirring. Afterwards, PEG-400 was added at 0.5 mL PEG/10 mL of solution. Then, an acidic chitosan solution (0.5% w/v) of low molecular weight was added at a ratio of 0.5 mlL/10 mL of sodium nitrite solution. In a different container, acidic solution of tetramethylorthosilicate (2.5 mL/0.6 ml HCl) was prepared and sonicated in ice bath, then added to the NO-donor solution (1 mL tetramethylorthosilicate/10 mL solution). The obtained mixture was then stirred and set aside for gelation, followed by freeze drying. The control nanoparticles were prepared using the same procedures but without the NO-donor.

Figure 1B:
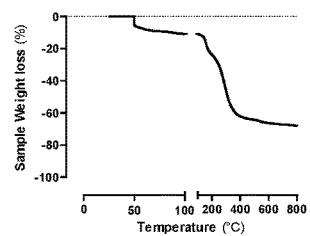
Figure 1C:
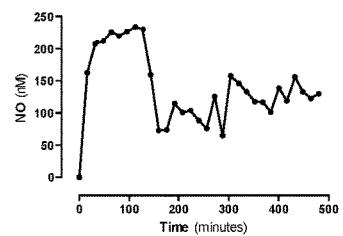
FIG. 1C shows particles were also assessed for NO release over a period of 8 hours.
Figure 1D:
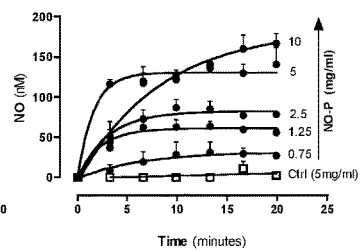
FIG. 1D shows NO release over 20 minutes from different concentrations of NO nanoparticles (0.75, 1.25, 2.5, 5, and 10 mg/ml) compared to control plain nanoparticles (at 5 mg/ml)

The nanoparticles were characterised by powder X-ray diffraction (FIG. 1A) and themogravimetric analysis (FIG. 1B). Particles were also assessed for NO release over a period of 8 hours (FIG. 1C) and NO release over 20 minutes from different concentrations of NO nanoparticles (0.75, 1.25, 2.5, 5, and 10 mg/ml) compared to control plain nanoparticles (at 5 mg/ml) (FIG. 1D). It can be seen that the majority of NO is released in the first 100 or so minutes, while higher concentrations of nanoparticles release more NO.

Figure 2A:
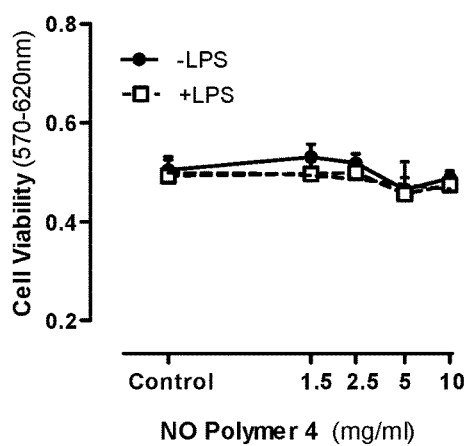
FIGS. 2A and 2B demonstrate the effect of the developed NO nanoparticles on cell viability (FIG. 2A) and release of the chemokine CXCL8 (FIG. 2B) from endothelial cells grown from blood of healthy donors with or without stimulation with LPS.
Figure 2B:
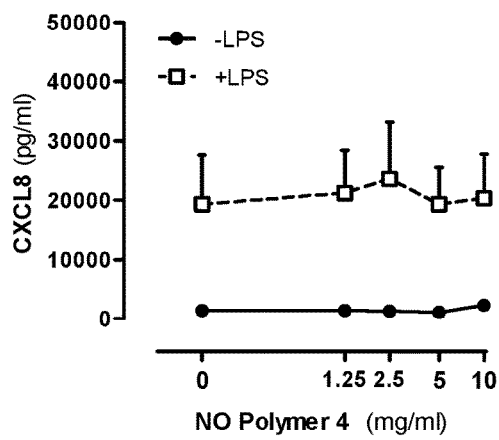

FIGS. 2A and 2B demonstrate the effect of the developed NO nanoparticles on cell viability (FIG. 2A) and release of the chemokine CXCL8 (FIG. 2B) from endothelial cells grown from blood of healthy donors with or without stimulation with LPS. The NO-releasing nanoparticles were contacted with the cells at concentrations of 1.5, 2.5, 5, and 10 mg/ml.

Figure 3A:
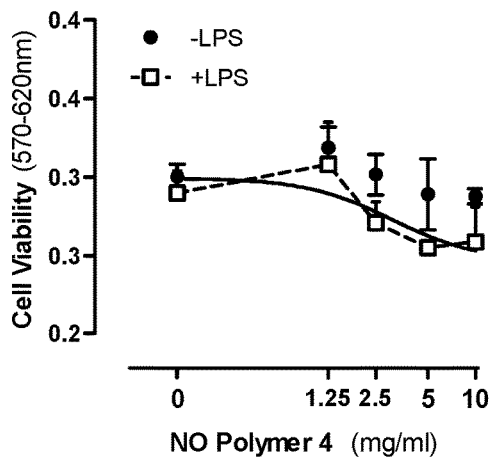
FIGS. 3A and 3B show a similar experiment to FIGS. 2A and 2B, using pulmonary artery smooth muscle cells (PAVSMCs) in place of endothelial cells.
Figure 3B:
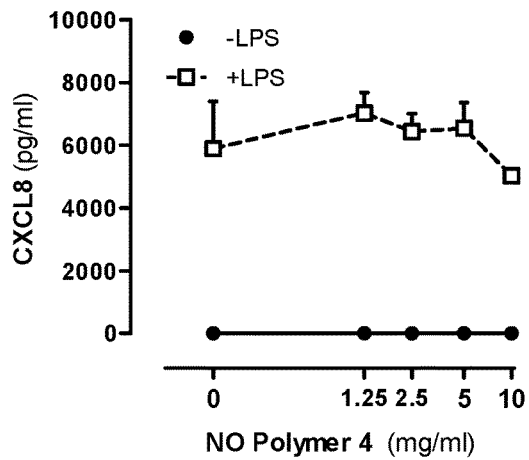

FIGS. 3A and 3B show a similar experiment to FIGS. 2A and 2B, using pulmonary artery smooth muscle cells (PAVSMCs) in place of endothelial cells.

Figure 4A:
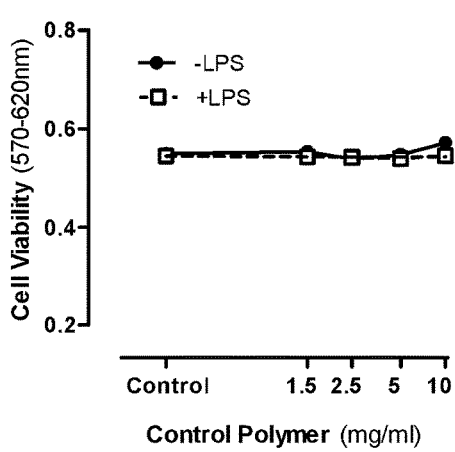
FIGS. 4A and 4B show the effect of control nanoparticles on viability (FIG. 4A) and release of the chemokine CXCL8 (FIG. 4B) from endothelial cells grown from blood of healthy donors with or without stimulation with LPS.
Figure 4B:
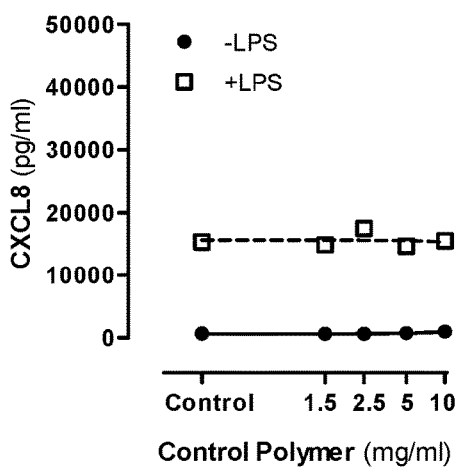

FIGS. 4A and 4B show the effect of control nanoparticles on viability (FIG. 4A) and release of the chemokine CXCL8 (FIG. 4B) from endothelial cells grown from blood of healthy donors with or without stimulation with LPS. Nanoparticles were contacted with the cells at concentrations of 1.5, 2.5, 5, and 10 mg/ml. There is essentially no effect of the nanoparticles lacking NO.

Thus, these experiments demonstrate that appropriate NO-releasing agents can be incorporated into nanoparticles and that these nanoparticles will confer a sustained release of therapeutic levels of NO.

Nanoparticles may be incorporated into a biodegradable stent as follows. A porous polymer scaffold may be produced by PELT, so as to leave pores in the polymer scaffold. The scaffold is then dip coated in a polymer coating; the coating solution includes the NO-releasing nanoparticles. The scaffold is repeatedly dipped into the solution, and the polymer coating allowed to set, until the desired coating thickness is reached.

As the polymer coating degrades in the body, the nanoparticles will contact the lumen and begin to release NO. This will last for the duration of the degradation of the coating, as new nanoparticles are released from the coating. To further prolong the release of NO, nanoparticles may be incorporated into the scaffold too; this will typically degrade more slowly than the coating, and hence allow a continued release of NO.

REFERENCES (1) Gogas, B. D. Bioresorbable Scaffolds for Percutaneous Coronary Interventions. *Global Cardiology Science and Practice* 2014.
(2) Voûte, M. T.; Gonçalves, F. M. B.; van de Luijtgaarden, K. M.; Nulent, C. G. K.; Hoeks, S. E.; Stolker, R. J.; Verhagen, H. J. Stent Graft Composition Plays a Material Role in the Postimplantation Syndrome. *Journal of vascular surgery* 2012, 56, 1503-1509.

The invention claimed is:

1. A drug eluting bioresorbable stent, the stent comprising
a) a bioresorbable scaffold;
b) a bioresorbable polymeric coating disposed on the scaffold; and
c) nitric oxide (NO)-releasing nanoparticles incorporated into the polymeric coating, and into the scaffold.

2. The stent of claim 1, wherein the nanoparticles comprise a polymer and an NO donor.

3. The stent of claim 2 wherein the nanoparticles further comprise a sugar.

4. The stent of claim 3 wherein the sugar comprises one or more sugars selected from sucrose, trehalose, tagatose, and glucose.

5. The stent of claim 3 wherein the sugar is glucose.

6. The stent of claim 4, wherein the sugar comprises sucrose, trehalose, tagatose, and glucose.

7. The stent of claim 2 wherein the NO donor is a nitrite.

8. The stent of claim 2 wherein the polymer is a hydrogel polymer.

9. The stent of claim 2 wherein the polymer is a swellable polymer.

10. The stent of claim 2 wherein the polymer comprises one or more polymers selected from polyethylene glycol (PEG), polyvinylpyrolidone (PVP), alginate, polyethylene oxide, polyvinyl alcohol (PVA), polyvinyl acetate (PVAc), polycaprolactone (PCL), poly(ethylene-co-vinylacetate) (PEVA), poly(butyl methacrylate) (PBMA), poly (L-lactide) (PLLA), poly (D-lactide) (PDLA), poly (D,L-lactide) (PDLLA), poly(3-hydroxybutyrate), poly(4-hydroxybutyrate), poly(glycolic acid), poly(lactic-co-glycolic acid) (PLGA), a chitosan or a chitosan derivative polymer.

11. The stent of claim 2 wherein the polymer comprises PVP, PEG-400, and chitosan of low molecular weight.

12. The stent of claim 1 wherein the nanoparticles, scaffold, and/or the coating further comprise one or more additional therapeutic agents.

13. The stent of claim 12 wherein the additional therapeutic agent is selected from everolimus, tacrolimus, paclitaxel, and sirolimus.

14. The stent of claim 1 wherein the coating comprises a polymer selected from polyethylene glycol (PEG), polyvinylpyrolidone (PVP), alginate, polyvinyl alcohol (PVA), polyvinyl acetate (PVAc), poly(ethylene-co-vinylacetate) (PEVA), poly(butyl methacrylate) (PBMA), poly(lactic-co-glycolic acid) (PLGA), a chitosan or a chitosan derivative polymer, poly (L-lactide) (PLLA), poly (D-lactide) (PDLA), poly (D,L-lactide) (PDLLA), poly(3-hydroxybutyrate), poly (4-hydroxybutyrate), poly(glycolic acid), polycaprolactone, polyethylene oxide, tyrosine derived polycarbonates, and polyanhydride esters of salicylic acid or a combination of two or more of said polymers.

15. The stent of claim 14 wherein the coating comprises poly (D-lactide) (PDLA).

16. The stent of claim 1 wherein the scaffold comprises a polymer selected from polyethylene glycol (PEG), polyvinylpyrolidone (PVP), alginate, polyvinyl alcohol (PVA), polyvinyl acetate (PVAc), poly(ethylene-co-vinylacetate) (PEVA), poly(butyl methacrylate) (PBMA), poly(lactic-co-glycolic acid) (PLGA), a chitosan or a chitosan derivative polymer, poly (L-lactide) (PLLA), poly (D-lactide) (PDLA), poly (D,L-lactide) (PDLLA), poly(3-hydroxybutyrate), poly (4-hydroxybutyrate), poly(glycolic acid), polycaprolactone, polyethylene oxide, tyrosine derived polycarbonates, and polyanhydride esters of salicylic acid or a combination of two or more of said polymers.

17. The stent of claim 16 wherein the scaffold comprises poly (L-lactide) (PLLA).

18. The stent of claim 16 wherein the scaffold is porous.

19. The stent of claim 16 wherein the scaffold is produced by a particulate extrusion leaching technique (PELT), or by controlled expansion of saturated polymers (CESP).

20. The stent of claim 1 wherein the scaffold is a biodegradable metal scaffold.

21. The stent of claim 1 wherein the coating is provided on the scaffold by a dip coating technique.

22. The stent of claim 1 in combination with a delivery catheter.

23. The stent of claim 22 wherein the catheter is a balloon catheter.

* * * * *